(12) United States Patent
Hsu et al.

(10) Patent No.: US 6,884,627 B2
(45) Date of Patent: Apr. 26, 2005

(54) METHOD FOR ASCERTAINING THE QUALITY OF HERBS

(75) Inventors: Li-Wei Hsu, Taichung (TW); Su-Chen Chang, Taichung (TW)

(73) Assignee: Advanced Gene Technology, Corp., Taichung (TW)

( * ) Notice: Subject to any disclaimer, the term of this patent is extended or adjusted under 35 U.S.C. 154(b) by 117 days.

(21) Appl. No.: 10/116,811

(22) Filed: Apr. 5, 2002

(65) Prior Publication Data

US 2003/0190756 A1 Oct. 9, 2003

(51) Int. Cl.⁷ .............................................. G01N 33/566
(52) U.S. Cl. ...................... 436/501; 436/518; 436/164; 436/171; 435/5; 435/6; 435/7.1; 435/7.2
(58) Field of Search .................... 435/5, 6, 7.1, 7.2; 436/164, 166, 169, 171, 172, 161, 504, 518, 532

(56) References Cited

U.S. PATENT DOCUMENTS

| | | | |
|---|---|---|---|
| 6,156,291 A | 12/2000 | Pang et al. | 424/9.2 |
| 6,645,719 B2 | 11/2003 | Chang et al. | 435/6 |
| 2003/0138633 A1 | 7/2003 | Hsu et al. | 428/411.1 |
| 2004/0043478 A1 | 3/2004 | Hsu et al. | 435/287.2 |

FOREIGN PATENT DOCUMENTS

WO  WO 200224934  * 5/2000

OTHER PUBLICATIONS

Yun et al. "Epidemiological Study on Cancer Prevention by Ginseng:", J. Korean Med. Sci. ,2001, v.16 (Suppl); S19–27.*

Collins et al "A comparison of human immunodeficiency virus type 1 inhibition by partially purified aqueous extracts of Chinese medicinal herbs", Life Sciences (1997), 60(23), PL345–PL351.*

Budzinski et al "An in vitro evaluation of human cytochrome P450 3A4 inhibition by selected commercial herbal extracts and tinctures", Phytomedicine (2000), 7(4), 273–282.*

Carles et al. "Chips and Qi: microcomponent–based analysis in traditional Chinese medicine" Fresenius' Journal of Analytical Chemistry (2001), 371(2), 190–194.*

* cited by examiner

Primary Examiner—Yelena G. Gakh
(74) Attorney, Agent, or Firm—Morrison & Foerster LLP

(57) ABSTRACT

The present invention discloses a method for ascertaining the quality of herbs by applying the techniques of biochip for detecting the presence of biologically active, desired ingredient(s) in the herbs.

21 Claims, 7 Drawing Sheets

METHOD FOR ASCERTAINING THE QUALITY OF HERBS

TECHNICAL FIELD OF THE INVENTION

The present invention relates to a novel method for ascertaining the quality of herbs. In particular, the present invention applies the techniques of biochip for detecting the presence of biologically active, desired ingredient(s) in herbs.

BACKGROUND OF THE INVENTION

Herbs have been usually used as a whole plant for medical application for so many years. Herbs were typically ingested as an infusion or tea, or were applied externally as a poultice. It had been found, however, that there was significant variance in the medical effect among individuals of herbs of the same species, when the herbs were treated by the same way.

The ingredients of an herb were typically a mixture of many chemical compounds, and some of the chemical compounds might be biologically active and have a therapeutic effect on human and animals. The ingredients of an herb may vary in their compound species and/or the relative amount thereof, depending upon the genetic information of the individuals of the herb and the natural conditions when the herb grows, such as the geographic region for cultivation, soil composition, water quality, weather conditions including temperature and humidity, sunshine intensity, and growth period.

The effect of herbs for medical application to human and animals was dependent upon the presence of several active compounds and their relative amount contained in the herbs. The higher amount of the active compounds is present in an herb individual, the herb individual may exhibit a higher therapeutic effect. There was no scientific guideline to detecting the presence of desired, active ingredients in an herb and their relative amount, even when the herb had been known to have a specific therapeutic function. The quality of an herb individual having been known to have a therapeutic effect on human and animals was conventionally judged based on just the skilled people's experience in observing its body shape and color, in smelling its flavor and/or via chewing its tissue. There was no teaching in the art to ascertain by a scientific way the quality (i.e. the presence of desired, active ingredients and/or their relative amount) of herbs having a therapeutic effect on human and animals.

U.S. Pat. No. 6,156,291 disclosed a method of reproducibly extracting a pharmacologically active mixture of chemical components from a plant source, wherein there was an improved quality control of the mixtures of pharmacologically active components.

For ascertaining the quality of herb individuals for a specific medical application, the first demand in the art is to develop a scientific method for detecting and ascertaining the presence of active ingredients in the herb individuals, whereby those herb individuals having said active ingredients and in turn a desired, therapeutic effect could be screened, while other herb individuals, even including the herb individuals of the same species, which do not have said active ingredients, could be eliminated for use.

SUMMARY OF THE INVENTION

One aspect of the present invention provides a method for ascertaining the quality of herbs by applying the techniques of biochip for detecting the presence of biologically active, desired ingredient(s) in the herbs.

Another aspect of the present invention provides a method for ascertaining the quality of ginsengs cultivated in different regions by applying the techniques of biochip for detecting the presence of biologically active ingredients in the ginsengs that could specifically bind to tumor necrosis factor-$\alpha$.

DETAILED DESCRIPTION OF THE INVENTION

Figure 1A:
FIG. 1A shows the HPLC profile of a methanol extract of the powder of the crude trunk root of Pana ginseng C. A. Meyer cultivated in Korea, and the fluorescent image of the HPLC fractions.
Figure 1A:
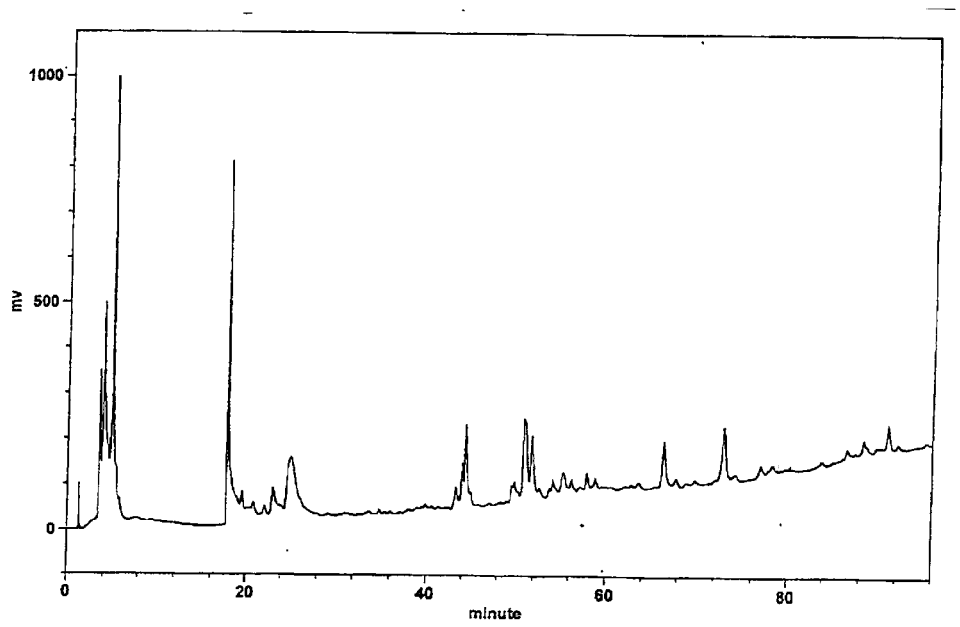
Figure 1B:
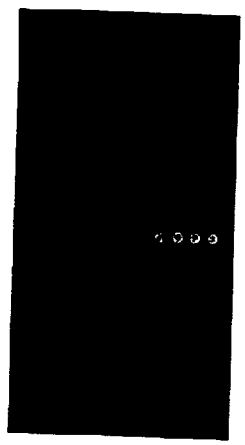
FIG. 1B shows the HPLC profile of a methanol extract of the powder of the slices of Pana ginseng C. A. Meyer cultivated at Kirin, the northeast region of China, and the fluorescent image of the HPLC fractions.
Figure 1B:
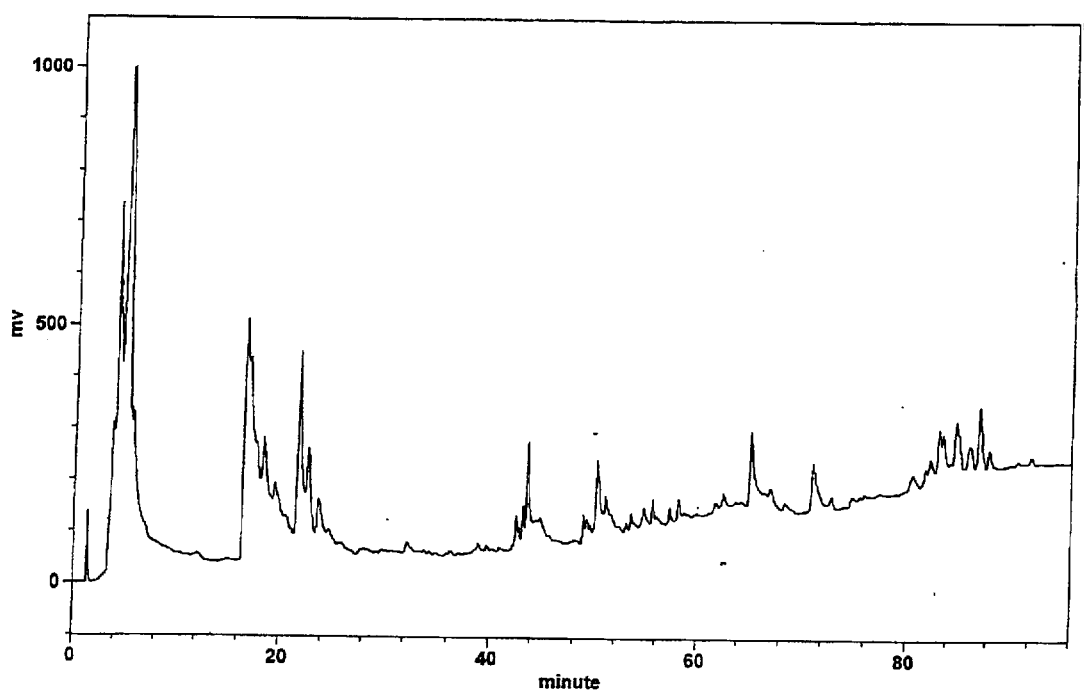
Figure 1C:
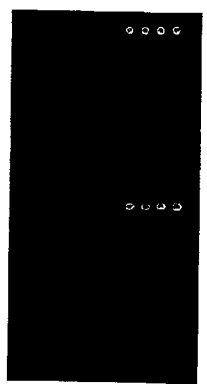
FIG. 1C shows the HPLC profile of a methanol extract of the powder of the slices of Pana ginseng C. A. Meyer cultivated in Korea, and the fluorescent image of the HPLC fractions.
Figure 1C:
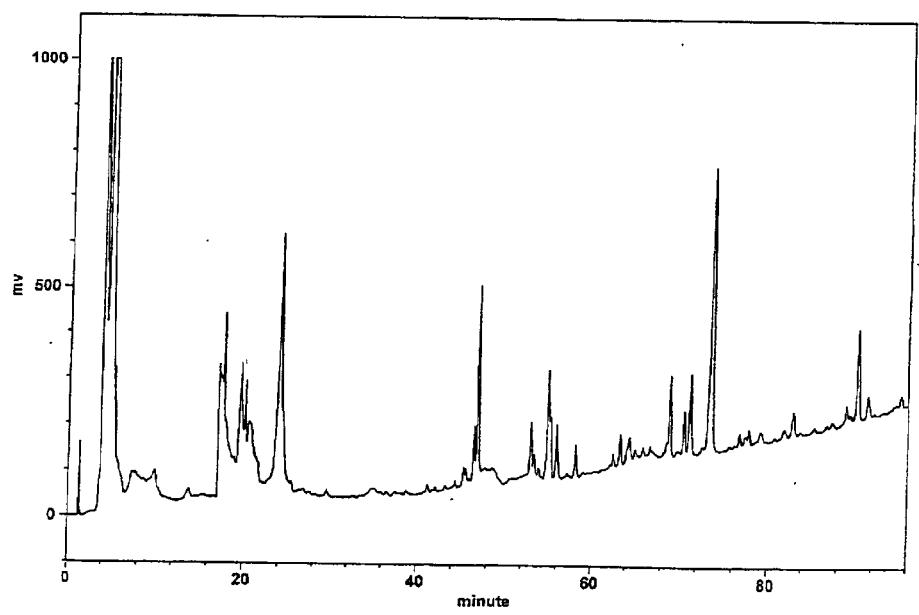
Figure 1D:
FIG. 1D shows the HPLC profile of a methanol extract of the powder of the slices of Pana ginseng C. A. Meyer cultivated in the Chang-Pai Mountain, the northeast region of China, and the fluorescent image of the HPLC fractions.
Figure 1D:
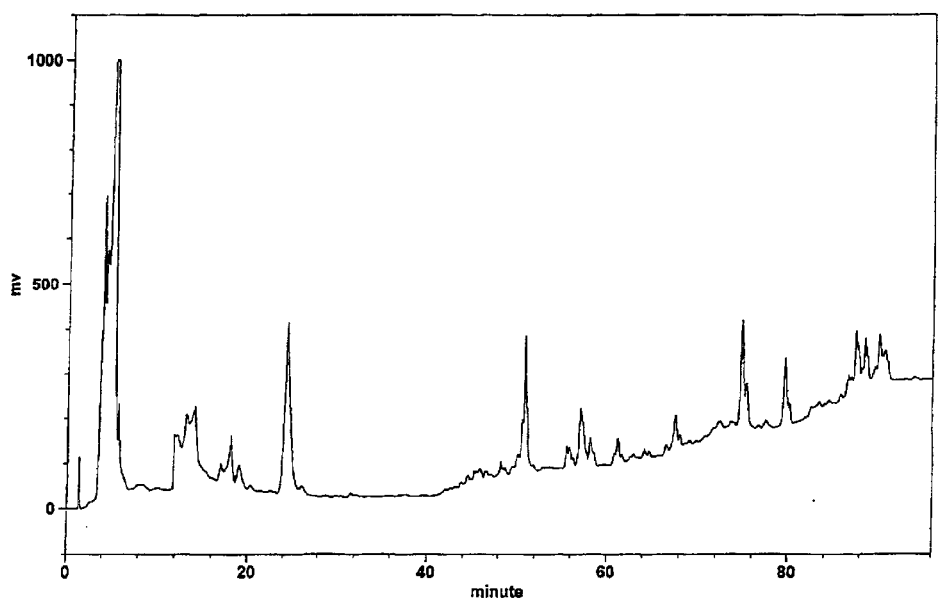

The present invention provides a method for ascertaining the quality of herbs by applying the techniques of biochip for detecting the presence of biologically active, desired ingredient(s) in the herbs.

The method of the present invention comprises the steps of fractionation of herb extracts with HPLC to obtain fraction samples of the herb extract, loading a coated plastic slide which has been pretreated, with the fraction samples of the herb extracts in microarray format, and conducting hybridization and signal detection.

The herbs were first ground into fine powders and extracted with a solvent. The solvent that may be used in the present invention includes water, $C_{1-6}$ alkanol, $C_{1-6}$ ether and a combination thereof. The herb extracts were then centrifuged, and the supernatants thus obtained were concentrated. The concentrated supernatants were fractionated by applying HPLC, while absorbance of the fractions was monitored. The resultant fractions were collected.

In the present invention, the plastic slide may be made of a homopolymer or copolymer, which is produced by polymerizing one or more monomers selected from the group consisting of ethylene, haloethylene, propylene, halopropylene, acrylate, methacrylate, butadiene, acrylonitrile, norbornene and styrene, wherein a homopolymer of styrene is preferred. The plastic slide may be also made of polycarbonate. The plastic slide used in the present invention is comparable in size to the one conventionally used for a microarrayer and a laser scanner. The advantage of using a plastic slide in the method of the present invention is that there are a variety of chemicals that can be used for treating the surface of a plastic slide, whereby not only macromolecules (such as proteins and DNAs) but also micromolecules (such as metabolites of herbs) can be immobilized on the surface of the plastic slide, in view of the fact that the conventional glass slide was used for immobilizing just macromolecules, such as proteins and DNAs. Further, upon molding, a plastic slide can have a shape as desired and is also effective in cost. In an embodiment of the present invention, the plastic slide has two cavity chambers. The samples obtained from fractions of herbs can be gridded to the surface of the chambers, and the chambers can be loaded with a probe(s)-containing solution for conducting hybridization. The depth of the two cavity chambers may be the same or different, and ranges from less than 0.03 mm to up to 0.5 mm. Further, upon molding, two bars may be respectively located at the opposite sides of each chamber for supporting a glass lid, wherein the glass lid is useful for preventing the evaporation or loss of the probe(s)-containing solution, with which the chambers are loaded.

In the pretreatment of the plastic slides and preparation of coated plastic slides, the plastic slides were pretreated with a polyfunctional aldehyde, followed by soaking the plastic slide in a solution of $NH_2$ group(s)-providing precursor, whereby the resultant plastic slides contain active amino groups on their surface. The $NH_2$ group(s)-providing precursor may be organic or inorganic, and may be selected from the group consisting of $NH_4OH$, primary amine, secondary amine and tertiary amine, wherein the aliphatic or aromatic part of the primary amine, secondary amine and tertiary amine may be useful as an additional spacer arm. Among the $NH_2$ group(s)-providing precursors, $NH_4OH$ directly providing free $NH_2$ group is preferred.

In the present invention, the coating on the plastic slides is made of polyfunctional molecules, e.g. polyfunctional epoxides, as a spacer. The polyfunctional epoxides act for linking the ingredients contained in herbs to the pretreated plastic slides. The active epoxy groups on one end of the polyfunctional epoxides react with the amino groups on the surface of the pretreated plastic slides, while active epoxy groups on the other end of the polyfunctional epoxides react with or absorb the ingredients contained in the herbs. In particular, those compounds in the ingredients of herbs that contain free hydroxyl, sulfhydryl or amino groups can form a covalent bond with the active epoxy groups on the other end of the polyfunctional epoxides, and consequently are attached onto the coated plastic slides. The polyfunctional epoxides preferably contain a long chemical chain of 6 to 24 carbon atoms, whereby the ingredients of herbs would not directly bind to the pretreated plastic slide. In the method of the present invention, the binding of each of sample spots to the coated plastic slide is persistent, even after stringent stripping. In the present invention, not only macromolecules (such as proteins and DNAs) but also small molecules (such as metabolites of herbs) can be immobilized in a homogeneous or heterogeneous manner on the surface of the coated plastic slides.

In the step of loading the coated plastic slides with fraction samples of the herb extracts in microarray format, the fraction samples of herb extracts were spotted and immobilized on the coated plastic slide in a gridded area in microarrays with a microarrayer by applying the high-density gridding technology, wherein each of sample spots may contain homogeneous or heterogeneous ingredients of herbs. In the method of the present invention, the integrating miniaturization technique can be used for increasing the density of samples gridded on the coated plastic slides.

In the method of the present invention, the detection of the presence of biologically active, desired ingredient(s) in herbs for ascertaining the quality of the herbs was based on a target-directed strategy, which comprises loading the chambers of the coated plastic slides with a labeled probe(s)-containing solution for conducting hybridization (wherein each of the chambers may be covered by a glass lid for preventing the evaporation of the labeled probe(s)-containing solution), and imaging and identifying the sample spots that react with or bind to the labeled probe with an apparatus, e.g. a laser scanner. The probes used in the method of the present invention may be homogeneous or heterogeneous, known targets based on a defined molecular mechanism, which may be, for example, small molecules, competitive ligands, or antibodies against, for example, the selected cells, receptors, enzymes, or proteins. The label within the probes may be a dye or a radioactive material.

An embodiment of the present invention provides a method for ascertaining the quality of ginsengs cultivated in different regions by applying the techniques of biochip for detecting the presence of biologically active ingredients in the ginsengs that could specifically bind to tumor necrosis factor-α (TNF-α). In particular, for use as a probe for conducting hybridization in the method of the present invention, TNF-α was labeled with biotin and strepavidin was labeled with Cy3. In accordance with the method of the present invention, if a signal indicating the binding of the ingredient(s) in a sample spot on the treated plastic slides to the biotinylated TNF-α is observed, there should be at least one candidate in the ingredients of the sample spot that exhibits a biological activity against TNF-α. The candidate may be useful in the treatment of autoimmune diseases, such as rheumatoid arthritis.

In effect, the method of the present invention can quickly detect the presence of biologically active, desired ingredients in herbs and ascertain the quality of the herbs by a simple way.

The following Examples are provided to further illustrate the method of the present invention, but the scope of the present invention should not be limited to the following Examples.

EXAMPLES

Example 1
Fractionation of Ginseng Extracts with HPLC

Dried ginsengs that were cultivated in different regions were obtained (see Table 1) and ground to fine powders, which were then packed under vacuum for a long-term storage. The ground powder of each of the ginsengs (50 g) was extracted by continuously blending with methanol (500 ml, HPLC grade) at room temperature for 5 min. with a homogenizer (OMNI). The resulting extracts were centrifuged at 8,000 rpm at 4° C. for 30 min., and the residues (pellets) were then extracted and centrifuged twice by the same way as mentioned above. The clear supernatants thus obtained were collected and then concentrated to a final volume of 30 ml by using a rotatory evaporator (Laborota 4000, HEIDOLPH). The concentrated supernatants were brought to a volume of 50 ml with a mixture of 50% water and 50% ethanol, followed by mixing for 20 min. with a magnetic stir bar. The resultant solutions were centrifuged at 8,000 rpm at 4° C. for 30 min. The clear supernatants thus obtained were further centrifuged at 12,000 rpm at room temperature for 10 min., and the resultant clear supernatants were then analyzed.

When analyzed by HPLC assay, the clear supernatants (0.1 ml) as obtained above were applied to TSK Gel ODS-80™ column (4.6 mm×15 cm, 5 μm packing, TOSOH) previously equilibrated with water, and then eluted with a gradient of 0–100% ethanol in double-distilled water for 96 minutes at flow rate of 0.75 ml/min.

Figure 1E:
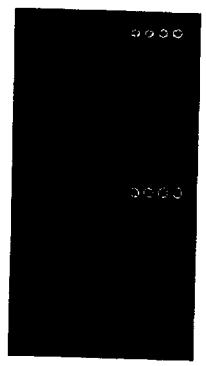
FIG. 1E shows the HPLC profile of a methanol extract of the powder of the slices of Pana ginseng C. A. Meyer cultivated in Wisconsin, U.S.A., and the fluorescent image of the HPLC fractions.
Figure 1E:
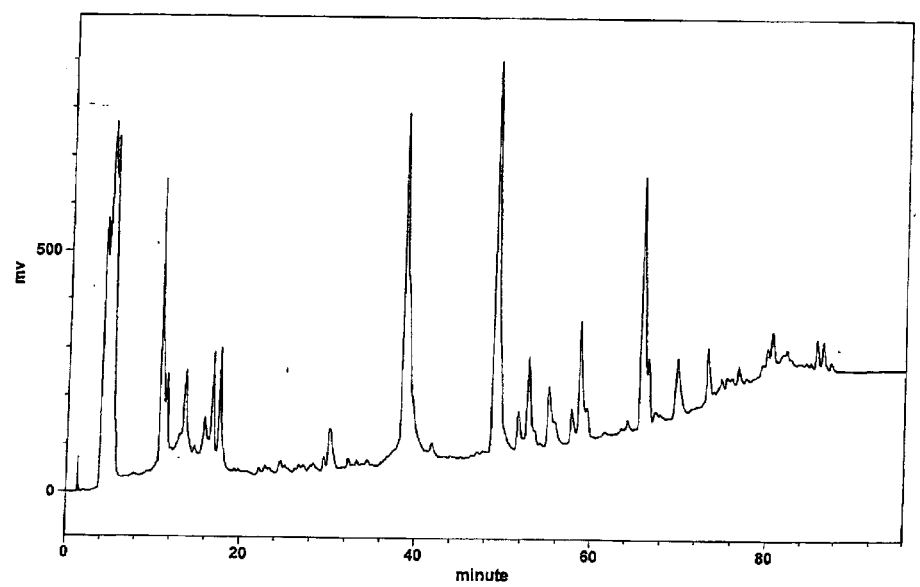

Absorbance of the eluates was monitored continuously at a wavelength of 205 nm. The results of absorbance were shown in the accompanying Figures, wherein FIG. 1E relating to the ginseng cultivated in Wisconsin, U.S.A. showed a distinguishable profile from the other profiles shown in FIGS. 1A, 1B, 1C and 1D, indicating that such difference in the HPLC profiles resulted from the different geographical regions for ginseng cultivation. The eluates were then collected with 0.75 ml/min./fraction from the time of 0 to 96 min., wherein 0.225 ml of each of the fractions that contained the ingredients of each of the ginsengs was transferred into each of the three 96-well round-bottom microtiter plates by using an automated liquid handling system (MultiProbe II, PACKARD). The resultant microtiter plates containing the dried ingredients of the ginsengs were available for conducting an activity assay or were ready for storage.

Example 2
Pretreatment of Plastic Slides and Preparation of Coated Plastic Slides Molded plastic slides were made of a polymer of styrene and comprised two cavity chambers. The molded plastic slide was comparable in size with the regular glass slide used for a microarrayer or laser scanner, wherein the depth of each of the cavity chambers was 0.05 mm.

The molded plastic slides were first immersed in 0.4% glutaldehyde solution (pH 5.0) for 4 hours at room temperature, followed by washing with water and then soaking in 3M $NH_4OH$ (pH 11.0) at 60° C. for 4 hours. The resultant plastic slides were then treated with 100 mM 1,4-butanediol diglycidyl ether (pH 11.0) at 37° C. overnight. The plastic slides thus obtained were washed with 0.1 M $NaHCO_3$ (pH 8.0) and was then dried.

Example 3
Loading the Coated Plastic Slides with Samples in Microarray Format

Microarrayer (BioGrid II, BIOROBOTIC) was used for spotting samples onto the coated plastic slides as obtained in Example 2. The dried ingredients of ginsengs contained in the microtiter plates as mentioned in Example 1 were dissolved in 30% DMSO/0.1M carbonate buffer, pH 9.5 for a final volume of 16 μl/well. A 4-pin (0.4 mm ID) tool was used for loading the surface of the cavity chambers of the coated plastic slides with the ginseng samples from the 96-well microtiter plates. A solution of biotin hydrazide (20 μg/ml) was spotted onto the surface of the cavity chambers of a coated plastic slide for use as a control. After the spots on the surface of the cavity chambers of the coated plastic slides were dried, the resultant plastic slides were treated by soaking with 1M ethanolamine (pH 8.0) at 37° C. for 2 hours.

Example 4
Hybridization and Signal Detection

Biotinylated tumor necrosis factor-α (B-TNFα) and Cy3-labeled strepavidin were used as a probe for conducting hybridization. Two glass lids (22 mm×22 mm) were used for respectively covering the two cavity chambers of each of the treated plastic slides as mentioned in Example 3, prior to loading the chambers of the treated plastic slides with 20 μl B-TNFα in TBST buffer (0.5 μg/ml, containing 50 mM Tris-HCl, pH 7.3, 0.15 M NaCl and 0.05% Tween 20) and incubating at 37° C. for 2 hours. The plastic slides thus treated were washed 4 times with the TBST buffer, and then were dried at 37° C. and covered with the glass lids as mentioned above. Each cavity chamber was loaded with Cy3-labeled strepavidin (20 μl). The resultant plastic slides were then allowed to stand at 37° C. for 2 hours, followed by washing with the TBST buffer 4 times and then rinsing with double-distilled water 4 times. The plastic slides as obtained above were dried at 37° C., and then scanned by applying a laser scanner (GenePix4000, AXON). The images of the scanning were also shown in the accompanying Figures.

Figure 2A:
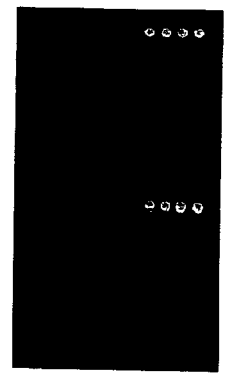
FIG. 2A shows the HPLC profile of a methanol extract of the powder of the slices of Pana notoginseng (Burk) Chen cultivated in the southwest region of China, and the fluorescent image of the HPLC fractions.
Figure 2A:
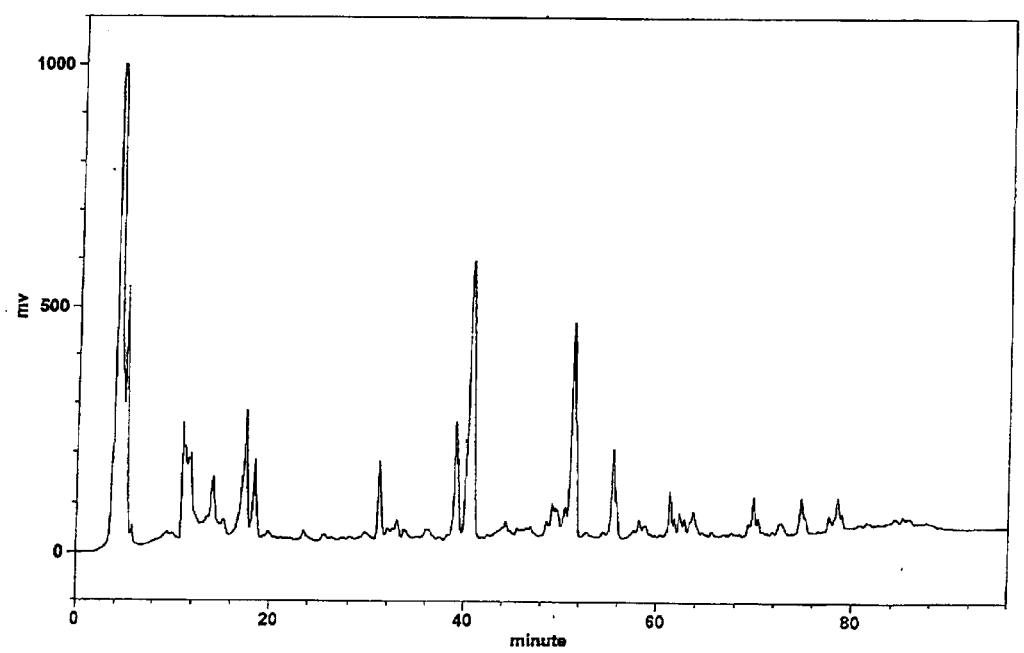
Figure 2B:
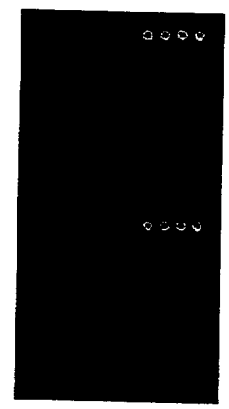
FIG. 2B shows the HPLC profile of a methanol extract of the powder of the crude trunk root of Pana notoginseng (Burk) Chen cultivated in the southwest region of China, and the fluorescent image of the HPLC fractions.
Figure 2B:
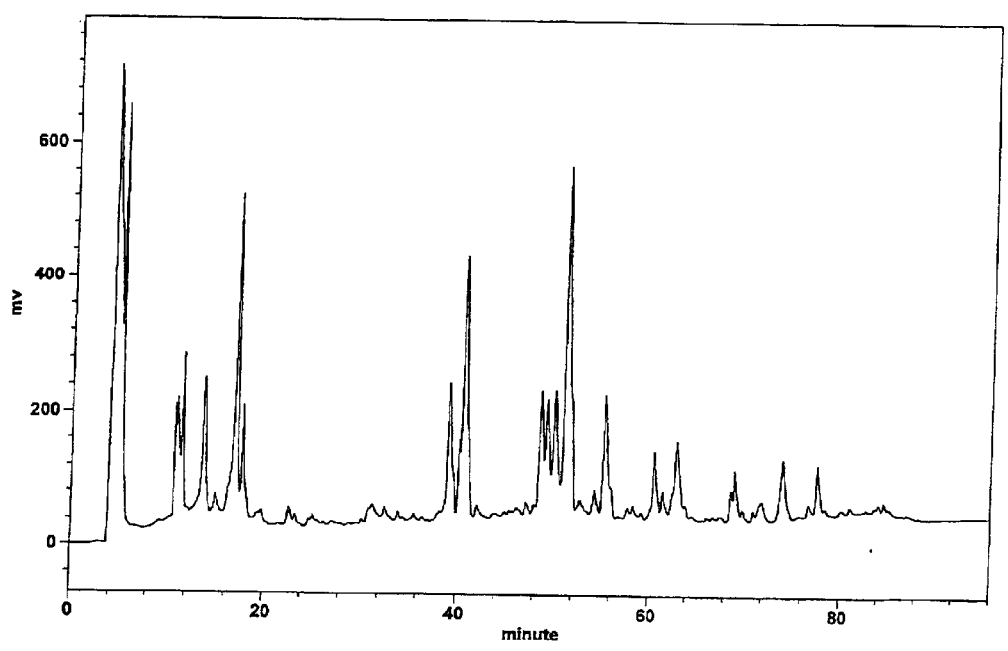

The green fluorescent spots on the images indicated that there existed at least one active ingredient in the ginseng samples that exhibited the binding activity to B-TNFα. From the results of the samples of Pana ginseng C. A. Meyer shown in the images, only the samples derived from the fractions 60–72 shown in FIG. 1A, i.e. derived from the crude trunk root of Pana ginseng C. A. Meyer cultivated in Korea, exhibited the binding activity to B-TNFα. The active ingredient in the fractions 60–72 that showed the binding activity to B-TNFα may be a ginsenoside, since ginsenosides are the major, biologically active compounds of Pana ginseng C. A. Meyer and have been known as an TNFα antagonist in murine or human macrophages (Planta Med. 2001 67; 213–218). Similarly, one of the two Burk ginseng samples that was derived from the fractions 3–16 shown in FIG. 2B, i.e. derived from the crude trunk root of Pana notoginseng (Burk) Chen, exhibited the binding activity to B-TNFα.

TABLE 1

| | Species | Geor aphical o irin | Appea ance | Firu es |
|---|---|---|---|---|
| 1 | Pana rinsenr C.A. Meye | Ko ea | C ude t unk oot | 1A |
| 2 | Pana rinsenr C.A. Meye | Ki in, China | Slices | 1B |
| 3 | Pana rinsenr C.A. Meye | Ko ea | Slices | 1C |
| 4 | Pana rinsenr C.A. Meye | The Chanr-Pai Mountain, China | Slices | 1D |
| 5 | Pana quinquefolius L | Wisconsin, U.S.A. | Slices | 1E |
| 6 | Pana notorinsenr (Bu k) Chen | The southwest of China | Slices | 2A |
| 7 | Pana notorinsenr (Bu k) Chen | The southwest of China | C ude t unk oot | 2B |

What is claimed is:

1. A method for ascertaining the quality of herbs, said method comprising the steps of fractionating herb extracts with HPLC to obtain fraction samples of the herb extract, loading a pretreated, coated plastic slide with the fraction samples of the herb extracts in microarray format, hybridizing the samples with a labeled-probe(s) specific for a biologically active, desired ingredient(s) in the herbs and detecting a labeled-probe signal for determining the presence of the biologically active, desired ingredient(s) in the herbs.

2. The method as claimed in claim 1, wherein the herbs are first extracted with a solvent selected from the group consisting of water, $C_{1-6}$ alkanol, $C_{1-6}$ ether and a combination thereof.

3. The method as claimed in claim 1, wherein the fractions of herbs obtained with HPLC are homogeneous.

4. The method as claimed in claim 1, wherein the plastic slide has two cavity chambers and the fraction samples are immobilized on the surface of the cavity chambers.

5. The method as claimed in claim 1, wherein the material of the plastic slides is a polycarbonate, or a homopolymer or copolymer that is made of one or more monomers selected from the group consisting of ethylene, haloethylene, propylene, halopropylene, acrylate, methacrylate, butadiene, acrylonitrile, norbornene and styrene.

6. The method as claimed in claim 5, wherein the plastic slide is made of a polymer of styrene.

7. The method as claimed in claim 1, wherein the plastic slide is pre-treated with a polyfunctional aldehyde, followed by soaking in a solution of $NH_2$ group(s)-providing precursor before coating the plastic slide.

8. The method as claimed in claim 7, wherein the polyfunctional aldehyde is glutaldehyde.

9. The method as claimed in claim 7, wherein the $NH_2$ group(s)-providing precursor is $NH_4OH$.

10. The method as claimed in claim 1, wherein the coating is made of polyfunctional molecules.

11. The method as claimed in claim 10, wherein the polyfunctional molecule is a polyfunctional epoxide containing at least one epoxy group at each of its ends.

12. The method as claimed in claim 11, wherein the epoxy group(s) at one end of the polyfunctional epoxide react with the amino group(s) on the surface of the pretreated plastic slide.

13. The method as claimed in claim 11, wherein the epoxy group(s) at the other end of the polyfunctional epoxide react with the free hydroxyl, sulfhydryl or amino groups of the ingredients contained in the herbs.

14. The method as claimed in claim 11, wherein the polyfunctional epoxide contains a long chemical chain of 6 to 24 carbon atoms.

15. The method as claimed in claim 1, wherein the herbs are ginsengs.

16. The method as claimed in claim 15, wherein the ginsengs are cultivated in different regions.

17. The method as claimed in claim 15, wherein the biologically active, desired ingredients in the ginsengs is the one that could specifically bind to tumor necrosis factor-α (TNF-α).

18. The method as claimed in claim 1, wherein a solution containing the labeled-probe(s) is used for the hybridizing.

19. The method as claimed in claim 18, wherein the labeled probe(s)-containing solution is heterogeneous.

20. The method as claimed in claim 19, wherein the label is a dye or a radioactive material.

21. The method as claimed in claim 18, wherein the labeled probe(s)-containing solution is homogeneous.

* * * * *